US009410952B2

(12) United States Patent
Schwertner et al.

(10) Patent No.: US 9,410,952 B2
(45) Date of Patent: Aug. 9, 2016

(54) METHOD AND DEVICE FOR THE DETERMINATION OF SEVERAL ANALYTES WITH SIMULTANEOUS INTERNAL VERIFICATION IN A GRAPHICAL COMBINATION

(75) Inventors: Heiko Schwertner, Schwerin (DE); Dorothee Monika Runge, Schwerin (DE)

(73) Assignee: DST DIAGNOSTISCHE SYSTEME & TECHNOLOGIEN GMBH, Schwerin (DE)

(*) Notice: Subject to any disclaimer, the term of this patent is extended or adjusted under 35 U.S.C. 154(b) by 1170 days.

(21) Appl. No.: 10/589,106

(22) PCT Filed: Feb. 16, 2005

(86) PCT No.: PCT/EP2005/001571
§ 371 (c)(1),
(2), (4) Date: Sep. 14, 2007

(87) PCT Pub. No.: WO2005/079135
PCT Pub. Date: Sep. 1, 2005

(65) Prior Publication Data
US 2008/0057595 A1    Mar. 6, 2008

(30) Foreign Application Priority Data
Feb. 17, 2004 (EP) .................... 04003497

(51) Int. Cl.
*G01N 21/01*    (2006.01)
*G01N 33/558*    (2006.01)
(Continued)

(52) U.S. Cl.
CPC ........ *G01N 33/54386* (2013.01); *G01N 33/521* (2013.01); *G01N 33/543* (2013.01);
(Continued)

(58) Field of Classification Search
CPC .......... G01N 33/558; G01N 33/54366; G01N 33/54386; G01N 33/543; G01N 33/521; G01N 33/525; G01N 33/5302; G01N 2035/00148; G01N 2035/00158; G01N 21/77; G01N 33/54306; B01L 2300/0816

USPC ............................................. 436/169; 422/55
See application file for complete search history.

(56) References Cited

U.S. PATENT DOCUMENTS 4,829,010 A  *  5/1989  Chang .......................... 436/518
4,943,522 A      7/1990  Eisinger et al.
(Continued)

FOREIGN PATENT DOCUMENTS

EP    0 451 686    10/1991
EP    0 505 632    9/1992
(Continued)

OTHER PUBLICATIONS

Burton W. Bials et al., "Multiplex enzyme immunoassay system for the simultaneous detection of mutiple allergens in foods", Food Control, vol. 14, pp. 43-47, 2003.
(Continued)

*Primary Examiner* — Jennifer Wecker
(74) *Attorney, Agent, or Firm* — Drinker Biddle & Reath LLP

(57) ABSTRACT

The invention relates to a device in which molecules capable of reacting with analytes that are to be detected are immobilized on a surface such that said analytes are bound and can be detected in a subsequent reaction or in several reaction steps. According to the invention, at least two such surfaces are combined in a graphically connected manner, one of said surfaces being used for detecting an analyte and the other one being used for verifying or quantifying the analyte. Said surfaces are embodied so as to simultaneously enter into contact with a sample matrix. The inventive device and a corresponding method can be used for all diagnostic areas, especially in medical diagnostics such as diagnoses of allergies, infections, typifications, DNA/RNA diagnoses, pharmacological and toxicological diagnoses, as well as in food diagnostics, veterinary diagnostics, or environmental diagnostics.

18 Claims, 5 Drawing Sheets

(51) Int. Cl.
*G01N 33/50* (2006.01)
*G01N 33/53* (2006.01)
*G01N 33/543* (2006.01)
*G01N 21/77* (2006.01)
*G01N 33/52* (2006.01)
*G01N 35/00* (2006.01)
*C12Q 1/68* (2006.01)

(52) U.S. Cl.
CPC ........ *G01N33/54306* (2013.01); *G01N 33/558* (2013.01); *B01L 2300/0816* (2013.01); *C12Q 1/6837* (2013.01); *G01N 21/77* (2013.01); *G01N 33/525* (2013.01); *G01N 33/5302* (2013.01); *G01N 33/54366* (2013.01); *G01N 2035/00148* (2013.01); *G01N 2035/00158* (2013.01)

(56) References Cited

U.S. PATENT DOCUMENTS

| | | | |
|---|---|---|---|
| 5,160,701 A * | 11/1992 | Brown et al. | 422/408 |
| 5,362,654 A * | 11/1994 | Pouletty | 436/518 |
| 5,401,667 A * | 3/1995 | Koike | G01N 33/558 422/412 |
| 5,707,818 A * | 1/1998 | Chudzik et al. | 435/7.93 |
| 5,976,813 A | 11/1999 | Beutel et al. | |
| 6,528,325 B1 * | 3/2003 | Hubscher et al. | 436/518 |
| 6,905,816 B2 * | 6/2005 | Jacobs et al. | 435/5 |
| 2002/0045195 A1 * | 4/2002 | Hubscher et al. | 435/7.9 |
| 2003/0148542 A1 * | 8/2003 | Pawlak et al. | 436/518 |
| 2003/0152994 A1 * | 8/2003 | Woudenberg et al. | 435/6 |
| 2003/0157699 A1 * | 8/2003 | Jerome et al. | 435/287.2 |
| 2005/0048506 A1 * | 3/2005 | Fredrick et al. | 435/6 |
| 2005/0070021 A1 * | 3/2005 | Lawrence et al. | 436/106 |
| 2005/0130120 A1 * | 6/2005 | Lambotte et al. | 435/4 |
| 2005/0249633 A1 * | 11/2005 | Blatt et al. | 422/56 |
| 2006/0029924 A1 * | 2/2006 | Brewster et al. | 435/4 |
| 2006/0134804 A1 * | 6/2006 | Gao et al. | 436/514 |

FOREIGN PATENT DOCUMENTS

| | | |
|---|---|---|
| EP | 1 376 131 | 1/2004 |
| WO | WO-94/03774 | 2/1994 |
| WO | WO-99/30154 | 6/1999 |

OTHER PUBLICATIONS

T, Kanbe et al., "A crossreactivity at the immunoglobulin E level of the cell wall mannoproteins of Candida albicans with other pathogenic Candida and airborne yeast species", Clinical and Experimental Allergy, vol. 27, pp. 1449-1457, 1997.

Christopher I. Baldwin et al., "Analysis of pigeon intestinal mucin allergens using a novel dot blot assay", Carbohydrate Research, vol. 326, pp. 43-49, 2000.

* cited by examiner

Figure 1a
Overall image when the analyte is present in the sample and the control indicates a positive result
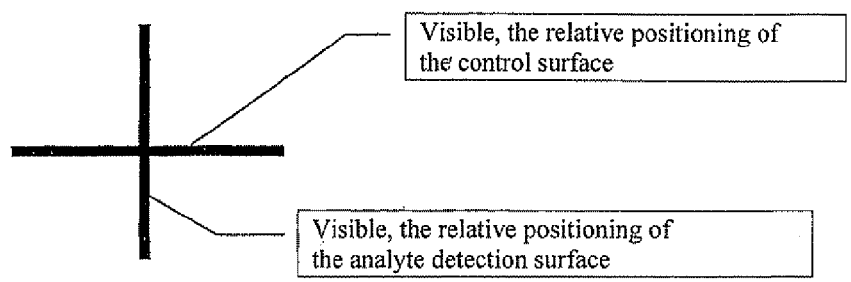
Overall image when the analyte is not present in the sample and the control indicates a negative result
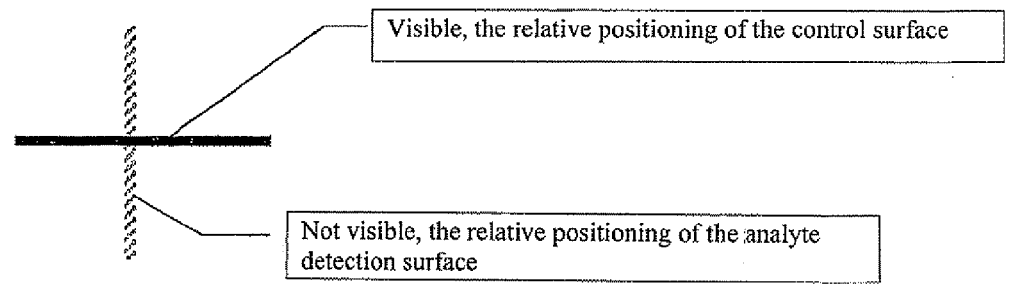
Figure 1b
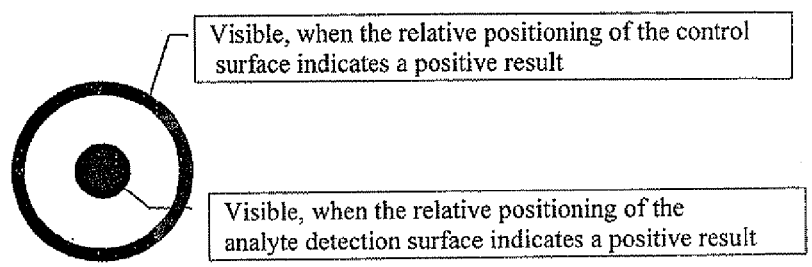

Figure 3

Inhalation panel

Test result of a person with multiple allergies, with a particularly strong reaction in D1 (mugwort pollen). The internal control is difficult to recognize at this position a

Inhalation panel

Test result of a person with multiple allergies, with a particularly strong reaction to hazel bush pollen and birch pollen (B1, 2) as well as to mugwort pollen (D1).

b

Food panel

Test result of a person with multiple allergies, with a particularly strong reaction to hazelnut (A2), peanut (B2), soy (C2), flour types (D2, A3), carrots (B3) and celery (C3).

c

Food panel

The test result is negative. The plus signs in row E belong to the positive controls.
E2: borderline
E3: positive d

METHOD AND DEVICE FOR THE DETERMINATION OF SEVERAL ANALYTES WITH SIMULTANEOUS INTERNAL VERIFICATION IN A GRAPHICAL COMBINATION

The present invention relates to a device to detect molecules or molecule classes or molecule mixtures in which at least two surfaces are chemically or physically modified on a panel of the device in such a way that said surfaces are provided with means to immobilize molecules or molecule classes and/or mixtures, whereby one surface is employed for control or standardization purposes, and the other serves to detect an analyte, whereby the two surfaces are structured in such a manner that they come into contact (Tangential-Touch-Test principle) at essentially the same point in time with an entire sample matrix from which molecules or molecule classes or molecule mixtures are to be tested for, and whereby both surfaces are structured and arranged with respect to each other in such a manner that they are evaluated together, thereby forming a graphic arrangement that can be read out visually. According to the invention, pairs of symbols can be rendered visible, "−" for negative and "+" for positive, or a circle for negative and a circle with a dot or dots in it for positive. Antibodies, antigens, DNA, RNA, enzymes, substrates, receptors, ligands or combinations thereof can be provided as the means for immobilizing molecules or molecule classes and/or mixtures.

BACKGROUND OF THE INVENTION

All of the references cited here are hereby incorporated in their entirety by reference for the purposes of the present invention.

In the fields of research, medicine, biology, chemistry, toxicology as well as many other areas of application, analytical laboratory tests that serve to qualitatively and/or quantitatively test for molecules or their activity or composition constitute the basis for in-depth statements, extending all the way to the development of new methods or devices. Examples of this are the analytical methods of molecular biology, which are employed in research, in forensic techniques for investigating crimes or else in medicine for detecting the presence of cancer. The basis for this comprises the generally known methods of DNA/RNA analysis or protein analysis. Another example is the wide array of analytical processes and methods that are employed to examine the antibody reactions, so-called immunoreactions, that serve to test for germs, proteins, drugs and many other substances. These analytical processes have one of broadest ranges of application areas. They are utilized in all fields of medicine, research, food product technology and pharmaceuticals.

Over the course of years, these laboratory techniques have been consistently refined through the wide range of analytical uses of DNA/RNA, proteins and other molecules. This has led to ever-greater success, further expanding the areas of application. The result of this is ever-higher numbers of samples that can be systematically examined for specific molecules. Since a large number of individual samples can be only be examined with considerable effort, so-called laboratory robots or, most recently, so-called chip technologies are used nowadays, which are capable of simultaneously examining up to several hundred samples.

In contrast to these demanding laboratory examination methods (EP 1 338 895, titled "High-density allergen microarray" or EP 0 875 758 B1, titled "Immunoassay") so-called fast tests that provide physicians and therapists with fast, simple analysis results that are limited to the essential points are being employed more and more frequently. There is a great demand and it is growing continuously. These tests are often employed in the so-called "point of care" area, that is to say, immediately before, during or after therapeutic measures. Another objective is to provide a cost-efficient alternative to classic laboratory tests. However, the reliability of the application and/or the number of analytes that can be tested for simultaneously as well as the analytical precision are all greatly limited. There is a considerable need for improvements in this realm.

Fast test methods are known such as the lateral-flow test (LFT), the flow-through test (FTT), the agglutination test (AT) and the solid-phase test (SPT). All of these methods serve to quickly detect analytes without the use of instruments and they are suitable for visual evaluation. All of these methods have drawbacks and can therefore only partially replace laboratory tests or else can only be employed by laypersons to a limited extent. This is why these methods are sometimes augmented by technical aids. Examples of these methods can be found, among other places, in the patent specifications DE 197 21151, EP 98 928 264.5, WO 98/53321, titled "Streifentest zur in vitro Allergiediagnostik" [Strip test for in vitro allergy diagnosis]; EP 1 369 391; WO 96/10747, titled "Device and method utilizing arrays of structures for analyte capture"; WO 03/094716; US 2003-212316, titled "Method and apparatus for determining blood parameters and vital signs of a patient"; WO 02/084249, titled "Therapeutic and diagnostic uses of antibody specificity profiles"; WO 00/40967, titled "Method and device for diagnosing allergy symptoms"; WO 02/066602, EP 135011.1; WO 93/10458, titled "Binding of milk allergens to a solid phase"; U.S. Pat. No. 6,528,325, WO 02/056017, titled "Method for the visual detection of specific antibodies in human serum by the use of lateral flow assays"; EP 1327884, titled "Reagent test strip comprising control means and timer means"; WO 97/31268, titled "Chromatographic strip having detection and control zones oriented parallel to the direction of flow"; U.S. Pat. No. 6,040,195, titled "Diagnostic sanitary test strip"; U.S. Pat. No. 6,509,196, WO 01/50129, titled "Compensation for nonspecific signals in quantitative immunoassays".

LFTs are the most widespread fast tests. Here, the sample, for instance, serum or urine, is applied onto a surface. In a manner that is directly comparable to thin-layer chromatography, the liquid (sample) flows through a separating layer containing reagents such as, for example, marked antibodies, and subsequently it flows through a nitrocellulose layer. The nitrocellulose layer contains capture layers (in contrast to SPT, in which capture layers are present on the surface of the carrier) that bind marked antibodies and form a line that is visible to the eye. Such methods were described in the scientific literature before 1980, both for use in classic thin-layer chromatography and as a fast test. The only differences are in the use of a standardized reactor or of a separating layer that can be used universally multiple times.

FTT is comparable to column chromatography. Here, the sample (liquid) flows through layers of membranes and suction layers. Like with LFT, for example, antibodies that are capable of binding analytes are bound to the detection membrane. The bound analytes are rendered visible as dots by means of various detection reagents. Such methods are described in the scientific literature before 1980, both in their use as column chromatography and as a fast test. The only differences are in the use of a reactor or of a column that can be used universally multiple times.

The AT method is based on particles that are coated with antibodies and that are in a uniform layer. If a positive sample is added, the uniform layer is destroyed by cross-linking, which is visible with the naked eye in the case of strong reactions.

With the SPT method, also often referred to as the "dipstick" test, antibodies or antigens bind the analytes to a surface (in contrast to LPT, in which the analytes are bound in a surface) and subsequently detected by subsequent reactions. Depending on the detection method employed, the result can be a dot or surface that is visible to the naked eye. Such a method is the method described in European patent specification EP 98 928 264.5 (titled "Streifentest zur in vitro Allergiediagnostik" [Strip test for in vitro allergy diagnosis]. Such methods, however, have also been described in the scientific literature prior to 1980.

All of these methods have individual advantages and disadvantages. An ideal fast test should allow evaluation by the naked eye, it should be able to test for multiple analytes in one sample, it should have internal standards for function control, quality control and quantity determination and it should also allow laypersons to carry out the evaluation. Moreover, the test should be fast, in other words, it should be possible to carry it out within about 25 minutes or less, and it should also be inexpensive to produce.

LF tests can only determine individual analytes—and only in exceptional cases several analytes—in one sample since here the sample liquid has to flow through the membrane. Although a positive-negative control is possible here, a quantification cannot be carried out. The same applies to AT, FTT and SPT tests, which usually make use of an external standard such as a color card (see patent specification EP 98928264.5) or a grayscale. This is a drawback for a visual evaluation, that is to say, an evaluation with the naked eye, because faulty interpretations can easily occur in these cases. Moreover, the sensitivity is greatly diminished. The SPT, AT and FTT methods, which have been known since the early 1980s, offer the possibility of testing for numerous analytes in a grid (matrix) comparable to the later chip technologies in the laboratory. None of these methods, however, is capable of performing a function control, a quality control or a quantity determination in each of the grid dots, for instance, by means of an internal standard. This, however, is necessary since an irregular distribution of the sample liquid over the test surface leads to concentration differences in the analytes to be tested for on this particular surface. This necessarily gives rise to faulty interpretations. A standard series with or without a positive or negative control leads to this effect of the faulty interpretation at the edges of the grid dots or else due to external color cards or gray scaling.

Therefore, it is the object of the present invention to avoid the existing disadvantages of the prevalent procedures and methods from the realm of fast tests without losing the advantages of the classic laboratory test methods, including laboratory robots and/or chip systems. It is likewise the object to simplify the test methods to such an extent that they can even be carried out by laypersons. Another object is to allow the analyses to be carried out without and/or with only simple aids or instruments.

This object is achieved according to the invention by a device in which molecules are immobilized on a panel, said molecules being capable of reacting with the analytes being tested for, so that these are bound and can then be detected in a subsequent reaction or in several reaction steps. Such molecules are, for instance, antibodies, antigens, DNA, RNA, enzymes, receptors, lectins, proteins or peptides. The immobilization surfaces are arranged in such a way that a positive or negative control are in a direct spatial relationship with the analyte. An example that does not limit the scope of the patent is a circle with a dot in its center, for instance, ⊙ (see FIG. 1). The outer circle is the positive control, so it always has to appear. The dot in the center only appears when the analyte is present in the sample (figuratively: bull's eye). The concentration of the positive control on the ring can be coordinated in such a manner that it only becomes visible above a certain threshold value (cut-off value). This allows a visual quantification in each grid dot. If the analyte is present in the sample in a high concentration, the color of the center dot makes it clearly stand out against the outer ring. If the analyte is present in a low concentration, the color of the center dot is only slightly distinct from the outer ring and if the result is negative, the ring is empty. If several rings are employed, a standard series can be depicted, for instance, ◉ (see FIG. 2). The outer rings are standard concentrations with a defined cut-off, the center dot in the middle is the sample measuring dot. This example clearly shows that a direct graphic combination of standard (measuring surface) to the measuring dot (surface) yields a considerable degree of evaluation reliability and a higher amount of information.

Therefore, the invention presented in this patent specification makes it possible to set up a fast test method that can be employed universally in order to be able to test for a broad spectrum of analytes in one sample. Furthermore, one or more or else numerous analytes can be tested for in parallel. This can be done in any desired grid (matrix or array), for example, linear or square. Such arrangements with surfaces that fulfill defined tasks, be it actively or passively, can already be found in the early scientific literature of all technical fields and are therefore part of the state of the art; examples of these are dot blot arrays, microtiter plate (MTP) coordinate systems. According to the invention, internal standards are employed to carry out a function control, a quality control and/or quantity determinations in each grid dot, so that if the analytes to be tested for yield a concentration gradient over the grid, this does not give rise to faulty interpretations. With the appropriate selection of the detection reaction, for example, an enzyme immunoassay (EIA), a detection employing gold, selenium or latex particles bound to antibodies, the test can be evaluated with the naked eye, in other words, purely visually. Moreover, by means of simple aids, the test can also make use of detection methods such as fluorescence marking, electrochemical detection or spectroscopic methods.

Furthermore, an especially good evaluation reliability can be ensured by means of the graphic design of the standard vis-à-vis the sample. Here, generally understood symbols are employed, for instance, "+" for positive (analyte present) and "−" for negative (no analyte present). This was described for LFT in European patent specification EP 0 421 294 B1, but here only one analyte can be detected in the sample liquid and there is no possibility for quantification. In the test according to the invention, numerous analytes to be tested for can be represented in this manner and quantification is concurrently possible in each grid dot. Moreover, others forms of representation such as a ring with a dot inside it or a star can be selected.

Another non-limiting example is a star symbol (see FIG. 2). In this case, five of the six star spokes are positive controls (corresponding to a standard series of a laboratory test method). These are set in such a way that they each become visible above certain concentration thresholds (e.g. rising). If present in the sample, the analyte likewise becomes visible as a function of its concentration. The direct spatial combination of the measuring point (analyte point) and the controls (in this case a standard series) allows a concentration determination to be carried out reliably. The precision of the visual read-out can be set via the number of star spokes. The selection of the graphic representation depends on the subsequent application. The symbols "+", "−", a circle with a dot or a star have proven their worth whenever a test format is desired that can be evaluated purely visually, that is to say, with the naked eye. If a test format is desired that is to be evaluated by means of technical aids of any type whatsoever, a circle with a center dot and a square with a central cross have proven their worth. In particular, the evaluation with technical aids such as a CCD camera, fluorescence detection, electrochemical detection or other spectroscopic methods can also recognize and evaluate production-related errors since the carry-over of test material can easily be recognized on the basis of a loss of resolution between the graphic dots and this can then be automatically evaluated by computer. This is not possible with any of the chip variants, whether DNA, RNA or protein chips, since no direct, close spatial relationship was achieved. If the immobilization of molecules additionally makes use of surfaces that are smooth or whose pores are small or inactivated, then sample materials (sample matrices) such as whole blood, capillary blood, serum, plasma, urine, feces or samples having a high viscosity and/or a strong coloration can be used directly in the test method according to the invention without additional preparation methods. Moreover, cell suspensions, tissue biooptates or any kind of solution can be employed.

The device according to the invention is also characterized in that it is not a chromatographic method like the lateral flow test (LFT), flow-through test (FTT), nor is it a method like the agglutination test (AT) or solid-phase test (SPT), but rather, it is a tangential-touch test principle (TTT). With this type of method according to the invention, it is sufficient if the sample to be analyzed comes into contact with the immobilization surface and here it is irrelevant whether the sample is flowing, is at rest or is applied actively and/or passively onto the surface. The TTT principle differs especially in that, with this method, measuring surfaces and control surfaces can be simultaneously brought into contact with the samples, both in terms of time and space Thus, this is not possible for instance, with all of the so-called dipstick methods or chromatographic methods, since the wetting with the sample always takes place sequentially—a dipstick is dipped into the sample liquid or the sample is drawn chromatographically through materials or else materials flow through it. It is likewise not necessary to arrange the immobilization surfaces in such a way that they are optimally aligned with the direction of flow (for example, EP 0 421 294 B1), titled "Improved self-performing immunochromatographic device).

The combination of immobilized molecules on surfaces, irrespective of the type and shape or material, in delimited areas for purposes of detecting analytes and an additional, graphically coordinated immobilization surface or surfaces that are spatially close to each for purposes of function control and/or quantification at each analyte measuring point employing the tangential-touch-test principle has not been described up until now and it constitutes the device according to the invention.

The device according to the invention is augmented by a method according to the invention which is characterized in that the analyte bound through immobilized molecules can be tested for by means of a subsequent reaction or reactions which will be referred to below as a detection reaction or as detection reactions. The detection reagents needed to carry out the method can be present on the surface completely freely, for example, as a lyophilisate or in solution, or else they can be added partially or entirely in separate steps. The advantage of the device and of the method is that all classic detection methods can be employed such as antigen-antibody reaction, marked antibodies or antigens, biotin avidine, DNA or RNA probes, electrochemical detection methods or spectroscopic methods. The combination of these detection methods with the device according to the invention constitutes the method according to the invention.

The number and arrangement of the combined grid elements is only limited by the application or by the application purpose. In applications involving an exclusively visual evaluation, the resolution limit of the human eye is ultimately the limiting factor. In such an application case, formats with up to 100 grids have proven their worth. If technical aids are employed for the evaluation, then, depending on the technical method and complexity, up to 100,000 grid elements can be evaluated.

Before the background of what was said above, a first aspect of the present invention is thus a device to detect molecules or molecule classes or molecule mixtures which is characterized in that a) at least two surfaces are chemically or physically modified on a panel of the device in such a way that said surfaces are provided with means to immobilize molecules and/or molecule classes or mixtures, whereby one surface is employed for control or standardization purposes, and the other serves to detect an analyte, whereby b) the two surfaces are structured in such a manner that they come into contact (Tangential-Touch-Test principle) at essentially the same point in time with an entire sample matrix from which molecules or molecule classes or molecule mixtures are to be tested for, and c) whereby both surfaces are structured and arranged with respect to each other in such a manner that they are evaluated jointly, thereby forming a graphic arrangement that can be read out visually.

Therefore, the invention relates to a panel on which two surfaces have been chemically or physically modified in such a way that molecules or molecule classes and/or mixtures thereof can be immobilized on these surfaces, so that they then form the basis that serves for purposes of control or (internal) standardization on the one hand and to detect an analyte in a sample (corresponding to the sample matrix) on the other hand. The immobilization of test materials on a surface is known in the state of the art and depends on the test materials themselves and on the test surface. The immobilization can take place covalently or non-covalently and either directly or via chemical groups.

As already explained above, owing to the arrangement of the surfaces (or also of the measuring points, grid dots), the present test is capable of providing a function control, a quality control and a quantity determination in every grid dot, for instance, by means of an internal standard. This is advantageous since, in the case of an uneven distribution of the sample liquid over the test surface, concentration differences in the analytes to be detected occur over the surface. This inevitably leads to faulty interpretations. A standard series with or without positive or negative control further exacerbates this effect of faulty interpretations at the edge of the grid dots or else through external color cards or gray scaling. According to the invention, both surfaces are structured and arranged on the panel with respect to each other in such a way that they can be evaluated jointly, whereby this structuring allows them to form a visually readable graphic arrangement. Therefore, preference is given to a device according to the invention to test for molecules or molecule classes or molecule mixtures that is characterized in that the surfaces are arranged with respect to each other in a level manner, in a spatial manner and/or in solid form. In a likewise preferred manner, the surfaces are structured and arranged on the panel with respect to each other according to the invention in such a way that they can be visually evaluated together. Such a visual evaluation is done, for example, through graphically coordinated surfaces that are spatially arranged very close to each other.

According to the invention, the two surfaces are structured in such a way that they come into contact at essentially the same point in time with an entire sample matrix from which molecules or molecule classes or molecule mixtures are to be tested for. According to the invention, this is understood as the Tangential-Touch-Test principle. Moreover, with this type of method according to the invention, it is sufficient if the sample to be analyzed comes into contact with the immobilization surface and here it is irrelevant whether the sample is flowing, is at rest or is applied actively and/or passively onto the surface. Therefore, the TTT principle differs from other methods especially in that, with this method, measuring surfaces and control surfaces can be simultaneously brought into contact with the samples, both in terms of time and space.

According to the invention, the sample matrix from which the analyte or analytes is/are to be tested for can be present in liquid, solid or gaseous form or else in physical intermediate states or combinations thereof.

In another aspect of the device according to the invention to detect molecules or molecule classes or molecule mixtures, said device is characterized in that the surfaces are represented by one or several symbols linearly or in a matrix arranged in a different manner.

In yet another aspect of the device according to the invention to detect molecules or molecule classes or molecule mixtures, said device is characterized in that the immobilized molecules or molecule classes and/or mixtures can be visually ascertained by means of a detection reaction without additional technical aids, whereby the various surfaces appear colored, black or gray, or are tinted in a mixture of colors and/or shades of gray.

Preference is given to a device according to the invention to detect molecules or molecule classes or molecule mixtures that is configured as a vessel having one or more openings. Preference is also given to a device according to the invention to detect molecules or molecule classes or molecule mixtures which is characterized in that the surfaces are located inside the vessel or else one or more surfaces are located on the vessel wall.

In yet another aspect of the device according to the invention to detect molecules or molecule classes or molecule mixtures, said device is characterized in that pairs of symbols are rendered visible, "−" for negative and "+" for positive, or a circle for negative and a circle with a dot or dots in it for positive.

In yet another aspect of the device according to the invention to detect molecules or molecule classes or molecule mixtures, said device is characterized in that the means for immobilizing molecules or molecule classes and/or mixtures are selected from the group consisting of antibodies, antigens, DNA, RNA, enzymes, substrates, receptors, ligands or combinations thereof.

The object of the present invention is also achieved by means of a method to detect molecules or molecule classes or molecule mixtures, said method comprising a) establishing contact between a sample matrix from which molecules or molecule classes or molecule mixtures are to be tested for, with the panel of a device in such a manner that they come into contact (Tangential-Touch-Test principle) at essentially the same point in time with the entire sample matrix from which molecules or molecule classes or molecule mixtures are to be tested for, whereby at least two surfaces are chemically or physically modified on the panel of the device in such a way that said surfaces are provided with means to immobilize molecules or molecule classes and/or mixtures, whereby one surface is employed for control or standardization purposes, and the other serves to detect an analyte, and whereby the two surfaces are structured and arranged with respect to each other in such a manner that they are jointly evaluated, thereby forming a graphic arrangement that can be read out visually, and b) a read-out and evaluation of the surfaces. Preference is given to a method according to the invention which is characterized in that the surfaces are read out in a planar manner, in a spatial manner and/or in solid form.

According to another aspect of the method of the invention, said method is characterized in that the various detection surfaces appear colored, black or gray, or are tinted in a mixture of colors and/or shades of gray. Preferably, the surfaces are read out in one or many symbols linearly or in a matrix arranged in a different manner. Examples of such arrangements are grid-like or checkerboard-like arrangements or an arrangement in a circle, other graphic symbols or letters or numbers. Likewise preferred is that symbols are rendered visible, "−" for negative and "+" for positive, or a circle for negative and a circle with a dot or dots in it for positive.

According to yet another aspect of the method of the invention, said method is characterized in that symbols consisting of several circles inside each other having one center dot are rendered visible, said dot appearing only in a positive detection case, and whereby each individual circle only becomes visible above a certain concentration value of the analyte or a star with which each of the spokes becomes visible above a certain concentration value and, in the positive case, a predefined spoke appears or the individual spokes detect the presence of several analytes and one spoke appears above a certain concentration value or a combination of these pairs of symbols.

According to yet another aspect of the method of the invention, said method is characterized in that the sample matrix from which the analyte or analytes is/are to be tested for, is present in liquid, solid or gaseous form or else in physical intermediate states or combinations thereof. Preference is given to the use of whole blood, capillary blood, umbilical cord blood, arterial or venous whole blood, serum, plasma, urine, feces, tears, saliva, body mucus, dyed solutions, solutions containing solid constituents or high-viscosity liquids as the sample matrix.

Likewise preferred is for the sample to be prepared before, during or afterwards by means of purification, aliquotation, derivatization and/or isolation in order to be applied onto the panel according to the invention.

According to yet another aspect of the method of the invention, said method is characterized in that the detection reactions of molecules, molecule classes or molecule mixtures are selected from dye, radio nucleotide, antibody, DNA or RNA, biotin, avidine or enzyme detection reactions or combinations thereof.

Preference is given to a method of the invention in which the immobilized molecules or molecule classes and/or mixtures can be visually tested for by means of a detection reaction without additional technical aids. However, an alternative method of the invention can be characterized in that technical aids are employed for the read-out and/or evaluation in order to allow a visual evaluation, or else the method, for instance, densitometric methods, spectroscopic or electrochemical methods are combined with the read-out and/or evaluation according to the invention. The method according to the invention can also be characterized in that it is combined with flow-through tests, agglutination tests and/or solid-phase tests and it comprises one, several or many pairs of symbols. The method according to the invention can also be characterized in that it is combined with the fast lateral-flow test method, and it comprises two, several or many pairs of symbols.

A last aspect of the present invention then relates to the use of a device of the invention in order to detect molecules or molecule classes in human medicine, veterinary medicine or in plant diagnostics, food-product diagnostics, environmental diagnostics, forensic diagnostics, pharmacology, toxicology, in the case of allergies, diseases of the autoimmune system or of the metabolic system, infectious diseases, venereal diseases, parasitic diseases, detection of small molecules such as drugs, pharmaceuticals or metabolites, cell mediators, tissue typing, species typing, food typing, antigen typing, epitotyping and DNA or RNA detection. Preference is given to a method according to the invention for diagnosis immediately before, during or after a therapeutic measure.

The terms employed within the scope of the present invention have the following meaning (list of definitions insofar as these have not already been internationally stipulated. The abbreviations not listed below always refer to the international standards that have been stipulated or that are commonly employed):

1a—symbol of "cross"; FIG. 1b—symbol of "cross with dot"; FIG. 1c—symbol of "diamond with inner diamond"; FIG. 1d—symbol of "polygon with polygonal center"; and FIG. 1e—symbol of "triangle with dot".

FIG. 2 shows examples of graphic pairs of symbols with a graduated standard series, with or without negative control. FIG. 2a—symbol of "star with negative control"; FIG. 2b—symbol of "circle without negative control".

FIG. 3 shows examples of inventive embodiments of arrangements on the basis of two inhalation panels (FIG. 3a, b) and two food panels (FIG. 3c, d).

EXAMPLES

The method according to the invention can be combined with the known fast test methods such as the lateral-flow test (LFT), the flow-through test (FTT), the agglutination test (AT) or the solid-phase test (SPT). Moreover, all optical methods such as densitometric methods, spectroscopic or

| | |
|---|---|
| Aliquotation | division of liquids into smaller quantity units or volumes, for example, withdrawal of a smaller amount from a sample |
| Analyte | molecule or molecule group to be detected |
| AT | agglutination test |
| Purification | separation of liquids, particles, substance classes, cells or cell components, impurities |
| Derivatization | chemical or physical modification of a substance or substance class |
| FTT | flow-through test |
| Isolation | separation of a substance or substance class from a complex mixture, irrespective of whether it is present in a solid, gaseous or liquid phase or in a combination |
| LFT | lateral-flow test |
| Detection | testing for the presence of one or more of the molecules or molecule groups with or without quantification thereof |
| Parameter | synonym for analyte |
| Quantification | determination of the quantity of molecules or molecule groups |
| SPT | solid-phase test |
| Technical aid | the term technical aid refers to all simple means that are utilized for rendering results visible, for intensifying, modifying and evaluating purposes or a combination thereof. For example, films, light sources, all kinds of detectors, chemical or physical reactions that are used before, during or after the measurement. Eyeglasses that only serve to correct natural vision are not considered as technical aids. |
| Visual evaluation | assessment of a measured result exclusively visually or with the naked eye. In this context, eyeglasses are not considered as technical aids |
| Negative | the analyte is not in the sample or below a stipulated cut-off value |
| Positive | the analyte is in the sample and/or above a stipulated cut-off value |
| Matrix | synonym: array; any arrangement and number of surfaces that can be individually identified within a coordinate system, for instance, a classic checkerboard coordinate system or an MTP coordinate system |
| MTP | microtiter plates |
| Cut-off | concentration limit value above which, if the analyte is present, the result is to be considered to be positive when the result is evaluated |

The method according to the invention can be carried out in alternative technical ways that differ from each other and it can also be employed in combination with classic fast-test methods.

The invention will be explained in greater detail below with reference to the accompanying drawings. The examples are not to be construed as limiting the scope of the invention, but rather serve to show the possibilities of the method.

Figure 1C:
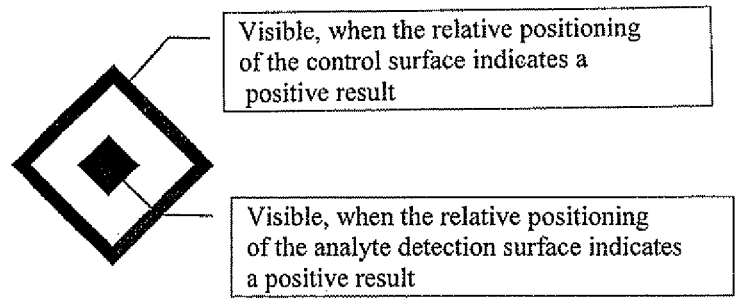
Figure 1D:
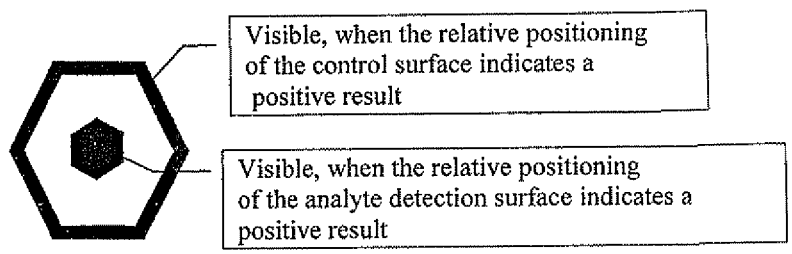
Figure 1E:
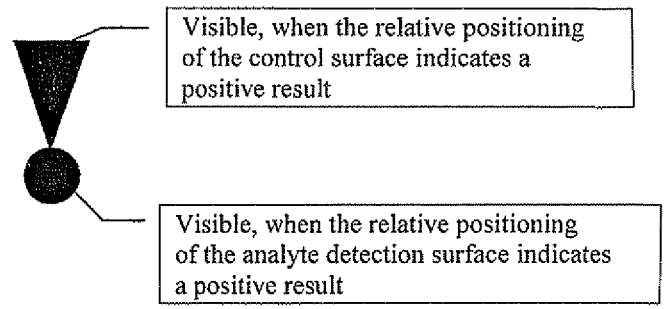
Figure 2A:
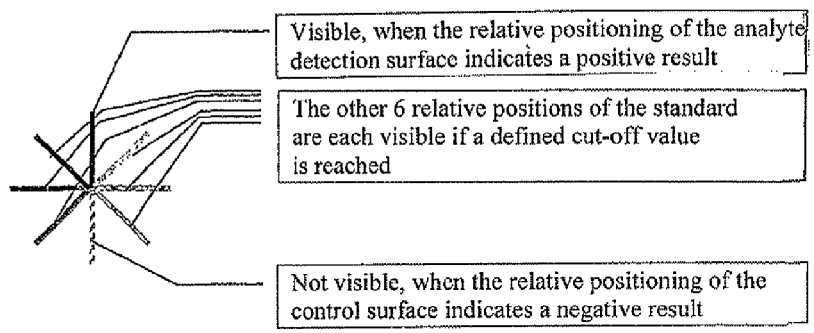
Figure 2B:
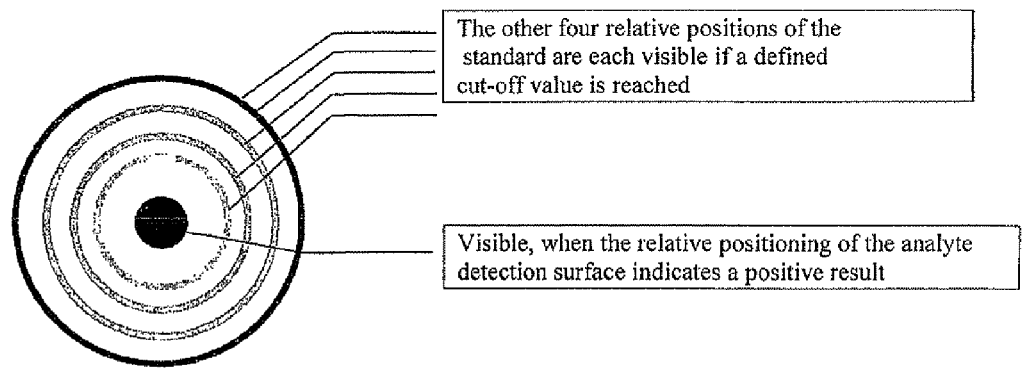
Figure 4:
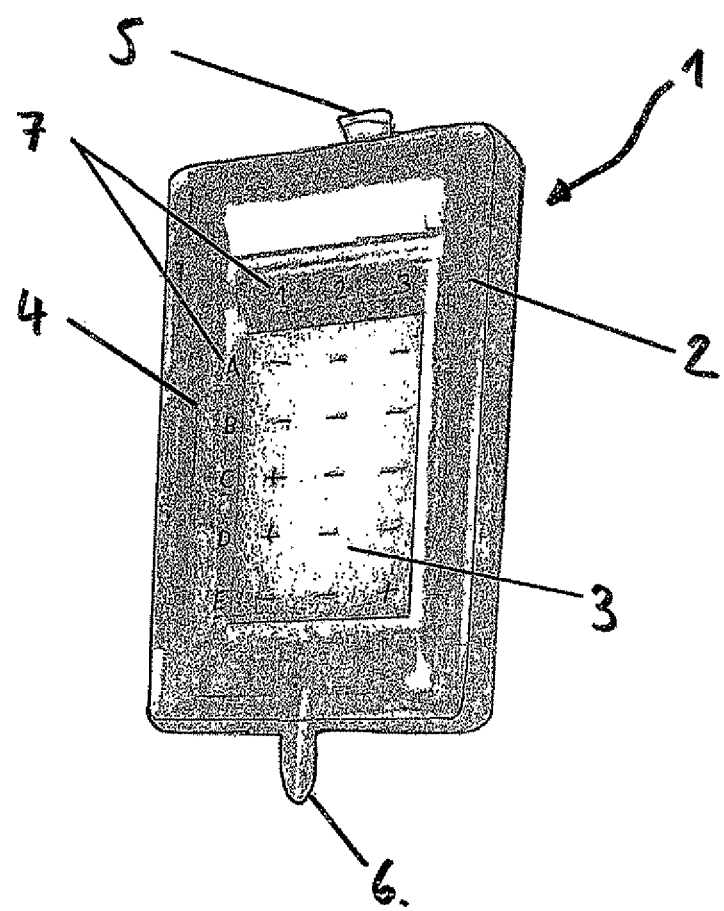
FIG. 4 shows an example of an inventive embodiment of a device (1) from Example 7, with a chamber (2), a membrane (3), a chamber cap (4), a chamber upper opening (5), a chamber lower opening (6) and a coordinate system (7).

FIG. 1 shows examples of graphic pairs of symbols with a simple positive control having a defined cut-off. FIG.

electrochemical methods can be combined with the method according to the invention. Examples of process-technology combinations are:

1. Antibody/antigen reactions, DNA or RNA probe reactions, enzyme/substrate reactions, receptor/ligand reactions or surface-affinity reactions or else combinations thereof can all be used to render symbols visible that are graphically directly connected, using the method according to the invention, irrespective of the level of sensitivity (visually or with technical aids). The selection of the detection reaction in only dependent on the analyte or analytes to be detected and on the conditions under which the detection is to take place.
2. Execution of the method with the device according to the invention employing a special vessel or without such a vessel.
3. Execution of the method with a purification, aliquotation, derivatization and/or isolation carried out before, during or afterwards.

The combination consisting of the device and the method according to the invention can be utilized for many areas of application, among others, human medicine or veterinary medicine diagnostics, food-product diagnostics, environmental diagnostics, forensic diagnostics. A few select examples will be presented below which serve to illustrate the scope of the patent but which should not be construed as a limitation thereof.

1. The combination consisting of the method and the device according to the invention can be used to test for patient-specific antibody or epitope profiles. Here, numerous different specific antibodies or epitopes found in the patient's body have to be tested for simultaneously. This is necessary in the case of diseases such as allergies or diseases of the autoimmune system or of the metabolic system.
2. The combination consisting of the method and the device according to the invention can be used to test for components of food products. This can be done in two directions, namely, on the one hand, testing for ingredients contained in a food product and, on the other hand, testing for individual food products in mixtures (processed food, etc.).
3. The combination consisting of the method and the device according to the invention can be used to test for infectious diseases, venereal diseases or parasitic diseases. Here, both germ-specific antigens and germ-specific antibodies can tested for on grids.
4. The combination consisting of the method and the device according to the invention can be used to test for metabolic diseases. Here, various metabolic enzymes and/or their metabolites can be simultaneously tested for in one test.
5. The combination consisting of the method and the device according to the invention can be used to test for small molecules such as drugs, pharmaceuticals, cell mediators or comparable small substances. These determinations are needed in pharmacology, toxicology and forensic analyses.
6. The combination consisting of the method and the device according to the invention can be used to test for DNA and/or RNA species. In this manner, for instance, genetically caused metabolic diseases can be tested for or viral infections can be detected in their early stages. Moreover, this allows all kinds of tissue typing, including those of humans, animals, plants and fungi.

Example 7

Example of a Device According to the Invention and its use

An example of a TTT device according to the invention and its use involves an allergy screening test for 12 food allergens by the physician with two drops of blood. In each case, 100 µl of EDTA blood, heparin blood or serum can also be employed. This test allows a fast overview of the allergens to which the patient reacts. A quantitative confirmation test as well as a test for other allergens can be subsequently performed. The method is roughly broken down into a) blood withdrawal (incubation time for the blood: 15 minutes); b) washing procedure (incubation time of the substrate: 5 to 10 minutes); c) second washing procedure; d) read-out; and e) evaluation.

Package Contents of the FastCheckPOC® Device According to the Invention 50 ml of washing solution, 300 µl of test solution, 3 ml of dye substrate
1×pipette, 1×lancet, 1×capillary tube, 1×10-ml plastic syringe, 1×5-ml plastic syringe
1×filter unit with 12 allergens and 3 controls
information on the test evaluation Preparations/Blood Withdrawal 1. Remove the capillary tube, the screw-top tube as well as the lancet from the package.
2. Open the brown 2-ml screw-top tube containing the test solution and set it upright on a level surface.
3. Withdraw the blood, for example, from the fingertip using, for instance, the lancet. Alternatively, 100 µl of EDTA blood, heparin blood or serum can also be used.
4. Remove the capillary from the clear tube and open the cap. Pick up two full drops of blood with the capillary. Add the blood to the screw-top tube containing the test solution. As a result, the blood is transferred to the test solution.

Test Execution

1. Open the bottle containing the washing solution and the chamber with the test filter and moisten the test filter with a small amount of the washing solution. A disposable pipette should be employed to distribute the liquid evenly.
2. Pick up the entire blood-test solution with the disposable pipette. Apply this solution onto the filter in the test chamber and distribute the solution on the membrane using the disposable pipette.
3. Close the chamber at first only as far as the small tab on the right-hand side of the test chamber can be closed. Flocculation of the blood does not detrimentally affect the result. However, no blood should be left behind on the chamber cap since otherwise the filter will not be adequately soaked. The incubation time is 15 minutes.
4. Completely close the test chamber. After complete closure, the chamber can no longer be opened. Remove the closure cap from the upper chamber opening.
5. In a first washing step, first rinse the test chamber with tap water. For this purpose, affix the syringe (10 ml) to the upper opening of the chamber and the water is evenly forced into the chamber. Hold the chamber with the lower opening above a sink or vessel into which the liquid can drain. Repeat the procedure 2 to 3 times. The filter may display a pink coloration. Pick up the rinsing solution with the syringe (10 ml) and inject it through the upper chamber opening into the housing by applying slow and steady pressure. Some of the washing solution remains in the chamber for 2 minutes, and only then is the syringe removed from the opening so that the liquid can drain completely. This procedure is repeated 2 more times. Subsequently, the test filter is rinsed twice with 10 ml of washing solution each time. Let the liquid drain.
6. Fill the small 5-ml syringe with substrate (black 3-ml bottle) and connect it to the chamber on the upper, large opening while holding the housing horizontal in this process in order to avoid air bubbles. Inject the substrate evenly into the chamber.
7. Lay the test chamber flat on a level surface. The chamber has to lie horizontal and the syringe should remain on the chamber opening so that the substrate cannot leak out. Incubate the substrate for 5 to 10 minutes in the chamber.
8. Remove the syringe and let the liquid drain from the chamber.

9. Fill with tap water using the large plastic syringe (10 ml) and connect the latter to the upper opening of the chamber.

10. Rinse the membrane with the contents of the syringe by holding the chamber with the second, smaller opening pointing downwards above a sink or vessel into which the rinsing liquid can drain. The procedure has to be repeated, but now some water should remain in the chamber in order to facilitate the read-out. The evaluation should be made within 10 minutes as long as the filter is still moist! If the waiting time is longer, non-specified subsequent reactions might occur that falsify the result.

Evaluation

1. The test filter has five rows in three columns. The bottom row contains, from the left to the right, a negative control, a limit value control and a positive control while the other four rows contain the allergens.

2. Evaluate the results on the basis of the coordinate system and transfer this to the evaluation form.

3. A minus sign means that the test is negative here, no allergies are present. A plus sign indicates a positive reaction, a specific IgE against the allergen in question is present. The position of the allergens is indicated on the evaluation form.

4. Mark the result in the appropriate column on the evaluation form.

LIST OF THE CITED PATENT LITERATURE

DE 19721 151, EP 98 928264.5, WO 98/53321, titled "Streifentest zur in vitro Allergiediagnostik" [Strip test for in vitro allergy diagnosis]

EP 0 421 294 B1 titled "Improved self-performing immunochromatographic device

EP 1 369 391; WO 96/10747, titled "Device and method utilizing arrays of structures for analyte capture"

WO 03/094716; US 2003-212316, titled "Method and apparatus for determining blood parameters and vital signs of a patient"

WO 02/084249, titled "Therapeutic and diagnostic uses of antibody specificity profiles"

WO 00/40967, titled "Method and device for diagnosing allergy symptoms"

EP 0875758 B1 Immunoassay

WO 02/066602, EP 1350111; WO 93/10458, titled "Binding of milk allergens to a solid phase"

EP 1338895, titled "High-density allergen microarray"

U.S. Pat. No. 6,528,325, WO 02/056017, titled "Method for the visual detection of specific antibodies in human serum by the use of lateral flow assays"

EP 1327884, titled "Reagent test strip comprising control means and timer means"

WO 97/31268, titled "Chromatographic strip having detection and control zones oriented parallel to the direction of flow"

U.S. Pat. No. 6,040,195, titled "Diagnostic sanitary test strip"

U.S. Pat. No. 6,509,196, WO 01/50129, titled "Compensation for non-specific signals in quantitative immunoassays"

The invention claimed is:

1. A device to detect molecules or molecule classes or molecule mixtures, comprising
    a) a panel comprising plurality of zones, wherein each zone comprises at least two surfaces with immobilized molecules or molecule classes are provided on the panel of the device, whereby a first surface is configured to be employed for control or standardization purposes, and a second surface is configured serves to detect an analyte, and wherein there is a difference between the immobilized molecules or molecule classes in at least two of the zones in the plurality of zones,
    b) whereby the at least two surfaces are configured to be in contact at the same point in time with an entire sample from which the one or more molecules or molecule classes or molecule mixtures are to be tested for, and
    c) wherein the at least two surfaces are arranged in a grid matrix or coordinate system in a planar and/or spatial arrangement on the panel with respect to each other and are configured to be evaluated by the naked eye without optical instruments,
    d) wherein the immobilized molecules or molecule classes are arranged on the surfaces to form symbols, and
    e) wherein each of the at first and second surfaces are configured to be rendered visible as two or more symbols arranged in a grid pattern configured to be evaluated by the naked eye without optical instruments, wherein each of the two or more symbols "−" for negative and "+" for positive, or a circle for negative and a circle with a dot or dots in it for positive, wherein the device is configured to allow for simultaneous evaluation of each immobilized molecule or molecule classes in the plurality of zones.

2. The device to detect molecules or molecule classes or molecule mixtures according to claim 1, characterized in that the sample from which the analyte or analytes is/are to be tested for is present in liquid, solid or gaseous form or else in physical intermediate states or combinations thereof.

3. The device to detect molecules or molecule classes or molecule mixtures according to claim 1, characterized in that the immobilized molecules or molecule classes are visually evaluated together by means of a detection reaction without additional technical aids, whereby the various surfaces appear colored, black or gray, or are tinted in a mixture of colors and/or shades of gray.

4. The device to detect molecules or molecule classes or molecule mixtures according to claim 1, characterized in that it is configured as a vessel having one or more openings.

5. The device to detect molecules or molecule classes or molecule mixtures according to any of claim 1, characterized in that the immobilized molecules or molecule classes and/or mixtures are selected from the group consisting of antibodies, antigens, DNA, RNA, enzymes, substrates, receptors, ligands or combinations thereof.

6. A method to detect molecules or molecule classes or molecule mixtures, comprising
    a) establishing contact between a sample from which molecules or molecule classes or molecule mixtures are to be tested for, with the panel of a device of claim 1 in such a manner that they come into contact at the same point in time with the entire sample from which molecules or molecule classes or molecule mixtures are to be tested for wherein the device is configured to allow for simultaneous evaluation of each immobilized molecule or molecule classes in the plurality of zones by the naked eye without the use of optical instruments.

7. The method according to claim 6, characterized in that the various detection surfaces appear colored, black or gray, or are tinted in a mixture of colors and/or shades of gray.

8. The method according to claim 6, characterized in that symbols consisting of several circles inside each other having one center dot are rendered visible, said dot appearing only in a positive detection case, and whereby each individual circle only becomes visible above a certain concentration value of the analyte or a star with which each of the spokes becomes visible above a certain concentration value and, in the positive case, a predefined spoke appears or the individual spokes detect the presence of several analytes and one spoke appears above a certain concentration value or a combination of these symbols.

9. The method according to claim 6, characterized in that the sample from which the analyte or analytes is/are tested for, is present in liquid, solid or gaseous form or else in physical intermediate states or combinations thereof.

10. The method according to claim 6, characterized in that whole blood, capillary blood, umbilical cord blood, arterial or venous whole blood, serum, plasma, urine, feces, tears, saliva, body mucus, dyed solutions, solutions containing solid constituents or high-viscosity liquids are used as the sample.

11. The method according to claim 6, characterized in that the sample is prepared before, during or afterwards by means of purification, aliquotation, derivatization and/or isolation in order to be applied onto the panel according to the invention.

12. The method according to claim 6, characterized in that the detection reactions of molecules, molecule classes or molecule mixtures are selected from dye, radio nucleotide, antibody, DNA or RNA, biotin, avidine or enzyme detection reactions or combinations thereof.

13. The method according to claim 6, characterized in that the immobilized molecules or molecule classes and/or mixtures are visually tested for by means of a detection reaction without additional technical aids.

14. The method according to claim 6, characterized in that technical aids are employed for the read-out and/or evaluation in order to allow a visual evaluation, or else the method, for instance, densitometric methods, spectroscopic or electrochemical methods are combined with the read-out and/or evaluation according to the invention.

15. The method according to claim 6, characterized in that the method is combined with flow-through tests, agglutination tests and/or solid-phase tests and it comprises one, several or many pairs of symbols.

16. The method according to claim 6, characterized in that the method is combined with the fast lateral-flow test method, and it comprises two, several or many pairs of symbols.

17. The device according to claim 1, wherein said molecules or molecule classes to be tested for are molecules or molecule classes in human medicine, veterinary medicine or in plant diagnostics, food-product diagnostics, environmental diagnostics, forensic diagnostics, pharmacology, toxicology, allergies, diseases of the auto-immune system or of the metabolic system, infectious diseases, venereal diseases, parasitic diseases, drugs, pharmaceuticals or metabolites, cell mediators, tissue typing, species typing, food typing, antigen typing, epitotyping and DNA or RNA detection.

18. The method according to claim 13, wherein said method is performed for diagnosis immediately before, during or after a therapeutic measure.

* * * * *